(12) United States Patent
Phelps et al.

(10) Patent No.: US 6,419,659 B1
(45) Date of Patent: Jul. 16, 2002

(54) LIPID POOL ASPIRATION ARRANGEMENT FOR THE TREATMENT OF VULNERABLE ATHEROSCLEROSIS PLAQUE

(75) Inventors: David Y. Phelps, Anchorage; Gregory Furnish, Louisville, both of KY (US)

(73) Assignee: MedVenture Technology Corp, Louisville, KY (US)

( * ) Notice: Subject to any disclaimer, the term of this patent is extended or adjusted under 35 U.S.C. 154(b) by 0 days.

(21) Appl. No.: 09/502,053

(22) Filed: Feb. 10, 2000

(51) Int. Cl.[7] .............................................. A61B 17/00
(52) U.S. Cl. ...................... 604/164.01; 604/35; 604/43; 604/164.09; 604/164.11; 604/264; 604/523
(58) Field of Search ................ 604/35, 43, 164.01, 604/164.06, 164.09, 164.11, 264, 523

(56) References Cited

U.S. PATENT DOCUMENTS

| | | | | |
|---|---|---|---|---|
| 5,628,761 A | * | 5/1997 | Rizik | 606/170 |
| 5,662,671 A | * | 9/1997 | Barbut et al. | 606/170 |
| 5,913,842 A | * | 6/1999 | Boyd et al. | 604/28 |
| 5,944,717 A | * | 8/1999 | Lee et al. | 606/48 |
| 6,090,135 A | * | 7/2000 | Plaia et al. | 623/1.11 |
| 6,165,199 A | * | 12/2000 | Barbut | 606/200 |
| 6,168,579 B1 | * | 1/2001 | Tsugita | 604/96.01 |

* cited by examiner

*Primary Examiner*—J. Casimer Jacyna
(74) *Attorney, Agent, or Firm*—Don Halgren

(57) ABSTRACT

The present invention comprises a vulnerable plaque treatment catheter arrangement for the treatment of a lipid pool at a site of vulnerable plaque within an artery. The catheter arrangement includes an elongated, hollow, flexible shaft having a proximal end and a distal end and an elongated, flexible, steerable, lipid-enterable needle arranged within the shaft. The needle has at least one lumen therethrough in communication with a treatment source, to permit the rendering of the lipid pool into an innocuous entity.

9 Claims, 1 Drawing Sheet

LIPID POOL ASPIRATION ARRANGEMENT FOR THE TREATMENT OF VULNERABLE ATHEROSCLEROSIS PLAQUE

BACKGROUND OF THE INVENTION

1. Field of the Invention

This invention relates to the treatment of vulnerable atherosclerosis and more particularly to an arrangement for the aspiration of a lipid pool within a coronary artery.

2. Prior Art

Atherosclerosis is the leading cause of coronary artery disease which may otherwise be called heart disease, which is the leading killer of men and women in the world today. It is characterized by deposits of fat, fibrin, cellular debris and calcium on the inside of arterial walls. The early stages of athersclorotic development is believed to occur as damage to the endothelial cells and tunica intima of the vessel wall. Once this damage has begun, the endothelial cells proliferate and attract a build-up of lipid substances. When these coronary arteries become blocked, symptoms ranging from angina to heart attacks, may occur. In a percentage of these cases, the coronary arteries may be unblocked through a non-invasive technique such as balloon angioplasty. Some five hundred to six hundred thousand angioplasties are performed each year within the United States. Where balloon angioplasty may not be appropriate, a bypass of the occluded or blocked vessel may be necessary. Identifying an opening such occlusions is known to give relief to the symtoms of angina, but it is also known that they do little to prolong life expectancy. The real killer in this coronary artery disease is often sudden blockages that are caused not by the slow accumulation of plaque that gradually block off the arteries, but by a sudden thrombosis (clotting) of the arteries caused by what are now referred to as "vulnerable plaque".

Vulnerable plaques are defined as plaques prone, in the presence of an appropriate trigger, to events such as ulceration rupture, erosion or thrombus that can lead to an acute syndrome. Those events are believed to share three common characteristics, a large lipid pool, a thin fibrous cap and macrophage infiltration.

Current methods of diagnosing arterial disease, using such as stress tests as angiograms, are inadequate at detecting these "vulnerable plaques". Therefore, in most instances, this potentially lethal condition often goes untreated.

It is an object of the present invention, to provide treatment options for this particular condition.

It is a further object of the present invention to provide a plaque treatment utilizing an improved catheter apparatus to minimize the accumulation and potential danger of lipids within an artery.

BRIEF SUMMARY OF THE INVENTION

The present invention relates to an aspiration/treatment catheter for the aspiration of a lipid pool within a coronary artery. The aspiration catheter comprises an elongated, flexible, polymeric shaft arranged to be pushed within a coronary artery. The aspiration catheter is hollow and enclosively supports an elongated needle. The needle is somewhat flexible, and functions as a guidewire to permit the advancement of the needle and catheter shaft to the situs of a lipid pool within a coronary artery.

The needle is flexible and steerable from the proximal end thereof, which proximal end extends outwardly from the proximal end of the aspiration catheter. The needle has a plurality of lumens therein. The first lumen is arranged to provide a suction at the distalmost tip of the needle, to a controllable vacuum source arranged in communication with the suction lumen at the proximal end of the needle. A second lumen is arranged within the steerable needle to function as a delivery conduit. The delivery conduit is arranged to bring a fluid or gas to the situs of the lipid pool, to permit the treatment of that lipid pool with a medicament or fluid agent.

A third lumen may be arranged within the steerable needle, which third lumen is arranged to contain an optic fiber. The optic fiber extends from the distal end of that steerable needle, within that needle, and proximally from the proximal and of the needle, to a monitor or eye piece, to be viewed by the operating physician. This permits the attending physician to steer the needle as necessary, and to apply medicaments and suction as needed.

In one preferred embodiment of the present invention, the steerable needle is movable longitudinally with respect to the catheter shaft. The steerable needle is preferably also movable rotationally with respect to that catheter shaft. The catheter shaft itself of course is advancable within the artery itself to the situs of the lipid pool.

In a further embodiment of the present invention, the aspiration catheter may have a position-indicating annular-band adjacent it's distalmost end, to provide the attending physician with means for determining the location of the catheter by magnetic or electromagnetic means.

Thus, in operation of the present aspiration catheter, upon insertion of that catheter within a coronary artery, and location of a lipid pool covered by a fibrous cap, as evidenced by the optical determination thereof, or other sensing means, the needle is steered and advanced so as to penetrate the fibrous cap and suction the lipid material from its pool beneath the fibrous cap and adjacent the artery wall. A treating agent may be injected within the fibrous cap to facilitate removal of the lipid therefrom or to promote healing of the artery wall once the aspiration catheter and steerable needle have been removed therefrom. The fluid introduced into the lipid pool may be a pharmaceutical agent to render the lipid non-thrombogenic or to facilitate its solidification.

The present invention thus comprises a vulnerable plaque treatment catheter arrangement for the treatment of a lipid pool at a site of vulnerable plaque within an artery. The catheter arrangement comprises an elongated, hollow, flexible shaft having a proximal end and a distal end; an elongated, flexible, lipid-enterable needle arranged within the shaft, the needle having at least one lumen therethrough in communication with a treatment source, to permit the rendering of the lipid pool into an innocuous entity. The needle is rotatable within the hollow shaft, to permit the catheter to be steered. The lumen in the needle may be connected to a vacuum source to permit the lipid pool to be suctioned through the needle by said vacuum source. The lumen in the needle may also be connected to a pressurized fluid source to permit the lipid pool to be treated by a liquid or gas medicament. The lumen in the needle is connected to an optical viewing apparatus by an optical fiber to permit the lipid pool to be monitored by an attendant. The needle may have a plurality of lumens therethrough, each in communication with a fluid pressure source and a suction source respectively to permit a lipid pool to be suctioned and medicated thereby. The sheath may have a position indicator band arranged adjacent its distal end to permit locating of the needle relative to a lipid pool.

The invention also includes a method of treating a vulnerable plaque in a coronary artery by the use of a vulnerable plaque treatment catheter arrangement comprising the steps of: arranging a movable hollow needle in an elongated flexible catheter sheath; extending a lumen through the needle, from a distal tip thereof, to a treatment source proximal of the catheter sheath; pushing the catheter into an artery to be treated, so the distal end of the needle reaches a lipid pool in the artery; piercing a fibrous cap of the lipid pool by the tip of the needle; and actuating the treatment source to as to effect treatment of the lipid pool by the catheter arrangement. The method may include the steps of: providing a vacuum at the treatment source so as to provide a suction at the distal tip of the needle in the lipid pool to draw the lipid therefrom; providing a fluid pressure at the treatment source so as to provide a fluid to be introduced into the lipid pool in the artery; arranging an optical fiber through the lumen so as to permit the lipid pool to be monitored visually; steering the catheter sheath into the artery by articulation of the needle with respect to the sheath; suctioning the lipid pool by a vacuum source at the proximal end of the lumen; and introducing a treatment fluid into the lipid pool from a pressurized treatment fluid source through a second lumen extending through the needle. The method includes the steps of: viewing the lipid pool through an optical fiber arranged through a third lumen in the needle, the fiber having a proximal end in communication with a viewing monitor; wherein the fluid introduced into the lipid pool renders the lipid pool inert or renders the lipid pool into a non-thrombogenic semisolid material.

By such treatment, vulnerable plaques, heretofore defined as plaques which are prone, in the presence of an appropriate trigger, to ulceration, rupture, erosion, or thrombus that can lead to an acute syndrome, may be rendered innocuous.

BRIEF DESCRIPTION OF THE DRAWINGS

The objects and advantages of the present invention will become more apparent, when viewed in conjunction with the following drawings in which.

DESCRIPTION OF THE PREFERRED EMBODIMENTS

Figure 1:
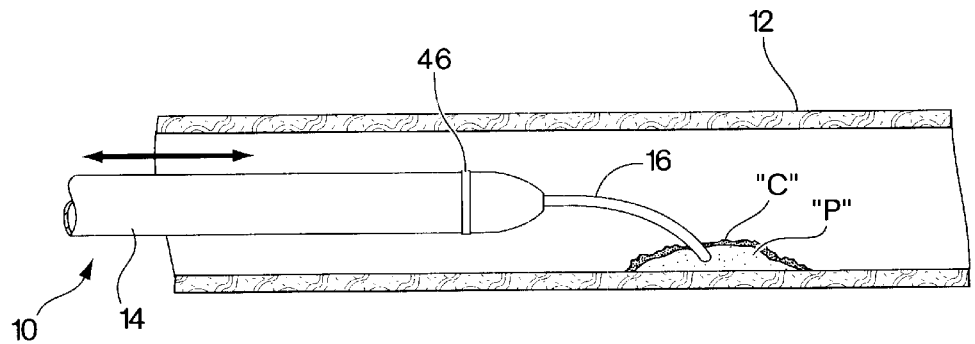
FIG. 1 is a side elevational view, in partial section, of an artery and an aspiration catheter constructed according to the principles of the present invention.

Referring now to the drawings in detail, and particularly to FIG. 1, there is shown the present invention which comprises an aspiration and treatment catheter 10 for the aspiration or medication of a lipid pool "P" within a coronary artery 12. The aspiration catheter 10 comprises an elongated, flexible, polymeric shaft 14 arranged to be pushed within a coronary artery. The aspiration catheter 10 is hollow and enclosively supports an elongated needle 16. The needle 16 is bendable and flexible, and functions as a guidewire to permit the advancement of the needle 16 and catheter shaft 14 to the situs of a lipid pool "P" within a coronary artery 12, and to pierce the fibrous cap "C" to enter the lipid pool "P".

The needle 16 is flexible and may be steered from the proximal end thereof (not shown for clarity of drawing), which proximal end extends outwardly from the proximal end of the aspiration catheter 10. The needle 16 has a plurality of lumens therein. A first or suction lumen 20 is arranged to provide a suction at the distalmost tip 22 of the needle 16, by a physician controlled vacuum source 24 arranged in communication with the suction lumen 20 by a vacuum line 28 at the proximal end of the needle 16. A second or delivery lumen 30 is arranged within the steerable needle 16 to function as a delivery conduit. The delivery lumen 30 is arranged to bring a fluid or gas from a pressurized fluid source 32, via a delivery line 34, to the delivery lumen 30, and out the tip of the needle 22 and into the lipid pool "P", to permit the treatment of that lipid pool "P" with a medicament or fluid agent.

Figure 2:
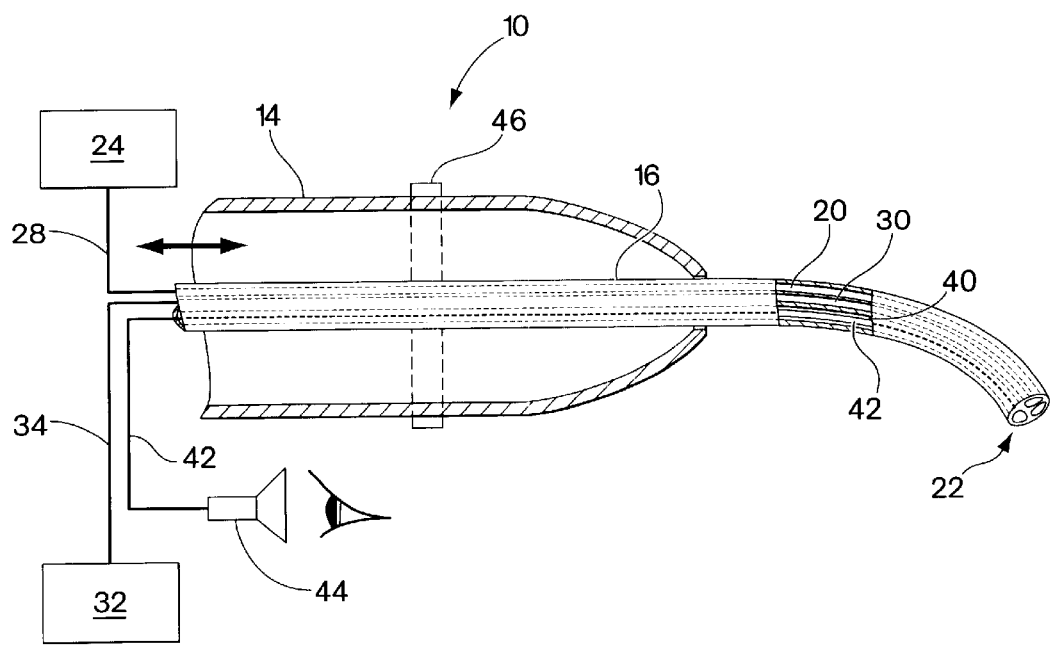
FIG. 2 is a side elevational view, in section of a aspiration catheter in conjunction with a control arrangement for the flexible needle therewith.

A third lumen 40 may be arranged within the steerable needle 16, which third lumen 40 is arranged to contain an optic fiber 42. The optic fiber 42 extends from the distal end 22 of that steerable needle 16, and within that needle 16, and thence proximally from the proximal end of the needle 16, to a monitor or eye piece 44, to be viewed by the operating physician, as may be seen in FIG. 2. This permits the attending physician to view the steering the needle 16 as necessary and if desired, unless other methods of guidance are desired, and to apply medicaments and suction as determined to be needed.

In one preferred embodiment of the present invention, the steerable needle 16 is movable longitudinally with respect to the catheter shaft 14. The steerable needle 16 is preferably also movable rotationally with respect to that catheter shaft 14 to provide guidance of that catheter 10 and needle 16 as it travels the twists and turns of an artery 12. The catheter shaft 14 itself of course is advancable within the artery 12 itself to the situs of the lipid pool "P".

In a further embodiment of the present invention, the aspiration catheter 10 may have a position-indicating annular-band 46 adjacent it's distalmost end, to provide the attending physician with means for determining the location of the catheter by magnetic or electromagnetic means.

Thus, in operation of the present aspiration catheter 10, upon insertion of that catheter 10 within a coronary artery 12, and location of a lipid pool "P" covered by a fibrous "cap", as evidenced by the optical determination thereof, or other sensing means, the needle 16 may then be steered and advanced so as to penetrate the fibrous cap "c" and suction or treat the lipid material from its pool "P" beneath the fibrous cap "c" and adjacent the artery wall. A treating agent may be injected within the fibrous cap to facilitate removal of the lipid therefrom or to promote healing of the artery wall once the aspiration catheter 0 and its steerable needle 16 have been removed therefrom. The fluid introduced into the lipid pool may be a pharmaceutical agent to render to the lipid non-thrombogenic or to facilitate its solidification.

By such treatment, vulnerable plaques, heretofore defined as plaques which are prone, in the presence of an appropriate trigger, to ulceration, rupture, erosion, or thrombus that can lead to an acute syndrome, may be rendered innocuous.

We claim:

1. A method of treating a vulnerable plaque in a coronary artery by the use of a vulnerable plaque treatment catheter arrangement comprising the steps of:

arranging a movable hollow needle in an elongated flexible catheter sheath;

extending a lumen through said needle, from a distal tip thereof, to a treatment source proximal of said catheter sheath;

pushing said catheter into an artery to be treated, so said distal end of said needle reaches a lipid pool in said artery;

piercing a fibrous cap of said lipid pool by said tip of said needle; and actuating said treatment source to as to effect treatment of said lipid pool by said catheter arrangement.

2. The method as recited in claim 1, including the step of:

providing a vacuum at said treatment source so as to provide a suction at said distal tip of said needle in said lipid pool to draw said lipid therefrom.

3. The method as recited in claim 1, including the step of:

providing a fluid pressure at said treatment source so as to provide a fluid to be introduced into said lipid pool in said artery.

4. The method as recited in claim 3, wherein said fluid introduced into said lipid pool renders said lipid pool inert.

5. The method as recited in claim 3, wherein said fluid introduced into said lipid pool renders said lipid pool into a non-thrombogenic semi-solid material.

6. The method as recited in claim 1, including the step of:

arranging an optical fiber through said lumen so as to permit said lipid pool to be monitored visually.

7. The method as recited in claim 1, including the step of:

steering said catheter sheath into said artery by articulation of said needle with respect to said sheath.

8. The method as recited in claim 1, including the steps of:

suctioning said lipid pool by a vacuum source at said proximal end of said lumen; and introducing a treatment fluid into said lipid pool from a pressurized treatment fluid source through a second lumen extending through said needle.

9. The method as recited in claim 8, including the step of:

viewing said lipid pool through an optical fiber arranged through a third lumen in said needle, said fiber having a proximal end in communication with a viewing monitor.

* * * * *